United States Patent [19]

Phalangas et al.

[11] Patent Number: 4,889,947

[45] Date of Patent: Dec. 26, 1989

[54] ULTRAVIOLET RADIATION ABSORBING NAPHTHALENYLIDENE COMPOSITIONS

[75] Inventors: Charalambos J. Phalangas; Thomas P. Cleary, both of Wilmington, Del.

[73] Assignee: ICI Americas Inc., Wilmington, Del.

[21] Appl. No.: 225,295

[22] Filed: Jul. 28, 1988

[51] Int. Cl.$^4$ .................................... C07C 69/608
[52] U.S. Cl. ........................... 560/119; 558/392; 558/394; 558/400; 558/405; 558/406; 558/408; 558/410; 558/426; 558/428; 560/37; 560/42; 560/43; 560/44; 560/45; 560/48; 560/51; 560/53; 560/54; 560/56; 560/80; 560/101; 562/441; 562/442; 562/444; 562/452

[58] Field of Search ............... 558/399, 327, 400, 394, 558/405, 406, 408, 428, 410; 560/37, 42, 43, 44, 45, 51, 48, 53, 54, 56, 80, 79, 101, 119; 562/442, 441, 444, 451, 452, 455, 462, 457, 466, 488, 491, 501; 564/152, 155, 158, 163, 169, 168, 172, 180, 188, 315, 321, 330, 428; 568/327, 633, 719

[56] References Cited

U.S. PATENT DOCUMENTS

| | | | |
|---|---|---|---|
| 2,894,936 | 7/1959 | Benson | 560/119 |
| 3,655,720 | 4/1972 | Leflingwell et al. | 260/464 |
| 4,418,087 | 11/1983 | Pittet et al. | 426/536 |
| 4,782,084 | 11/1988 | Vyas | 560/119 |

*Primary Examiner*—Michael L. Shippen
*Attorney, Agent, or Firm*—William E. Dickheiser

[57] ABSTRACT

Sunscreen compositions are described which contain certain substituted naphthalenylidenes which act as UV filters when incorporated in a carrier in amounts ranging from 0.1–50% by weight.

4 Claims, No Drawings

ULTRAVIOLET RADIATION ABSORBING NAPHTHALENYLIDENE COMPOSITIONS

The present invention is directed to ultraviolet absorbing compositions comprising certain novel naphthalenylidenes derivatives and blends thereof which are useful as protective coatings and to a method for protecting substrates against the harmful effects of actinic radiation in the UV range. It is further directed to a process for making ultraviolet absorbing coating compositions.

Ultraviolet radiation absorbing coatings are useful in protecting substrates such as plastic resins against accelerated deterioration and the skin of warm blooded animals against severe erythema, edema and blistering when exposed to sunlight. The compositions of the invention are generally referred to as sunscreen compositions and blends thereof can be incorporated with waxes, oils, lacquers, soft resins in the preparation of furniture and auto polishes, as well as cosmetics, suntan oils, lotions, lipstick, hair treatments, skin formulations, and in addition can be incorporated with contact lenses.

In particular, the invention relates to sunscreen compositions comprising a carrier having incorporated therein an effective amount of a filtering agent for ultraviolet radiation selected from compounds of the general formulas I and II:

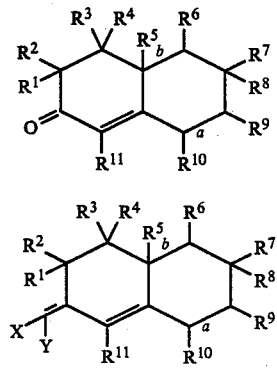

wherein:

X and Y are independantly selected from —CN, —COOR$^{12}$, —CONHR$^{12}$, —CON(R$^{12}$)$_2$, —PhCOOR$^{12}$, —PhCOR$^{12}$, —PhOR$^{12}$, —PhN(R$^{12}$)$_2$, or wherein only one X or Y is substituted with —H, and wherein:

R$^1$-R$^{11}$ are selected from H, —OH, —COOR$^{12}$, alkyl, alkoxy, or hydroxyalkyl groups having 1-5 carbon atoms and R$^{12}$ is selected from H, alkyl, alkylaryl or arylalkyl groups of 1-22 carbon atoms and Ph is a benzene ring.

Preferred compounds are those wherein X and Y are selected from —CN, —COOR$^{12}$, or —COR$^{12}$.

Most preferred compounds are those wherein X and Y are —COOR$^{12}$.

Of particular interest are compositions which provide selective absorption of actinic radiation in the 290-320 nm range as well as the 320-400 nm range of wavelength. The compounds may be present in the coating compositions as a finely divided solid or as a solute dispersed in an acceptable carrier when applied to a surface such that the selection of said carrier in the coating permits absorbency in the 290-400 nm range.

The compositions of the invention comprise the compounds of Formulas I and II in amounts needed to provide protection against the harmful effects of ultraviolet radiation. The amount or concentration of the compounds in the composition is such that when the composition is topically applied to a substrate the desired protection is provided. The amount needed to provide the desired protection can vary with the characteristics of the compound i.e., its extinction coefficient or substantivity, the nature of the carrier, the source and intensity of the radiation and other well recognized variables. Suitable amounts can be readily determined by standard methods of testing. Preferably the UV filter compounds are incorporated in the carrier in an amount ranging from about 0.1% to about 50% by weight and usually in amounts of 0.5-30% by weight and preferred 1.0%-15% by weight.

Carriers include any vehicle or medium capable of incorporating the UV filter compound in a manner permitting uniform topical application. For application on human skin, the carrier must be pharmaceutically acceptable. The term "pharmaceutically acceptable" is intended as a qualifier when the carrier is dermatologically innocuous to warm blooded animals and cosmetically acceptable. However, all carriers are not useful on animal skin. The carrier may comprise a wax, oil or cream base material in which the agent can be held in a clear solution or a uniform dispersion, for example, as submicron size particles. Preferably the carrier comprises a suitable solvent or a mixture of solvents capable of dissolving the UV filter compounds to provide a concentration that is effective as a sunscreen agent when incorporated in the sunscreen formulation. Solvents which may be useful include alcohols, ketones, esters, polyolesters such as oils, hydrocarbons, chlorinated hydrocarbons, ethers, polyethers, polyetherpolyols and other special solvents such as dimethylsulfoxide, dimethylformamide, dimethylisosorbide and the like. Such solvents are considered useful only if they do not permanently interact with the active filtering agents of the invention to shift the total effective absorption outside of the 290-400 nm range. Some of the above named ingredients are not pharmaceutically acceptable, but are useful in other applications.

The sunscreening compositions may be applied as a clear liquid or a lotion comprising a water-in-oil, or oil-in-water or a multiple emulsion. Either the oil or water base or both may be used as a carrier for the sunscreening compositions of the invention. The oil base material and the water and oil base compositions will form a continuous film of the UV filtering compound. Such films also provide long lasting protection against sun induced erythema. Sunscreening formulations are generally used in hot weather and at beaches where people enjoy bathing activities. It is therefore essential that the protective coating applied to the skin is not appreciably affected by water or perspiration. The compositions herein disclosed are included in a thin layer protective coating on the skin of warm blooded animals and provide long lasting protection against erythema and do not appreciably decompose over practical periods of exposure to sunlight.

Some of the compounds used as UV absorbers are known as flavoring agents such as in the case of the compounds of Formula I. Preparation procedures can be found in U.S. Pat. No. 3,655,720 and 4,418,087. These ketone derivatives can then be used as starting materials for various acetate, and malonate, diketone, or dibenzoyl derivatives of Formula II which are condensation products of naphthalenone with compounds having at least one activated methylene group.

The following preparative examples serve as non-limiting illustrations of the types of compounds and formulations included in the invention and all parts and percentages are expressed on a weight basis unless otherwise specified. Structural substituents are listed in Tables A and B.

PREPARATION 1

4,4,7-Trimethyl-4,4a,5,6-tetrahydro-2(3H)-naphthalenone

A mixture of isophorone (500 g, 3.62 mole), isopropenyl acetate (440 g, 4.34 mole) and p-toluenesulfonic acid (1 g) was heated in a distillation apparatus as acetone was slowly removed (10 hrs). The mixture was put under vacuum and the enol-acetate fractionally distilled while maintaining a pot temperature of 100°-120° C. Under these equilibrating conditions a 50-55% yield of desired enol-acetate isomer was realized. The product was isolated along with isophorone and undesired enol-acetate isomers.

To this enol-acetate mixture was added boron trifluoride etherate (3 mls) and the mixture put under nitrogen. Methyl vinyl ketone (MVK) (1.2 eq) was added slowly dropwise to maintain the pot temperature at 50°-60° C. (2 hrs). After addition, the isophorone was stripped off under reduced pressure and the crude Diels-Alder product added dropwise to 15% NaOH in methanol. After stirring for 4 hrs at room temp., the mixture was poured into brine, extracted with ethyl acetate, the organic phase dried (MgSO4) and the solvent stripped. The residue was vacuum distilled to yield the dienone 1.
Ref: U.S. Pat. No. 3,655,720.

PREPARATION 2

7-Methyl-4,4a,5,6-tetrahydro-2(3H)-naphthalenone

This material is prepared according to the procedure for Preparation 1 wherein 3-methyl-2-cyclohexenone is substituted for isophorone.
Ref: U.S. Pat. No. 4,418,087.

PREPARATION 3

6-Methyl-4,4a,5,6-tetrahydro-2(3H)-naphthalenone

6-Methyl-2-methoxy-2-methylchroman is reduced according to Preparation 9 wherein lithium in tetrahydrofuran (THF), t-butanol, and liquid ammonia is substituted for sodium in liquid ammonia. After hydrolytic workup, the resulting dione is cyclized in either acid or base to yield the dienone 3.
Ref: Tetrahedron Lett., 1971, 3803.

PREPARATION 4

4a-Methyl-4,4a,5,6-tetrahydro-2(3H)-naphthalenone 1,2,3,4-Tetrahydro-2-napthol is reduced according to Preparation 9. The resulting diene is cyclopropanated with Simmons-Smith reagent, oxidized with Jones reagent, then the cyclopropane ring opened with acid to form dienone 4.
Ref: J. Org. Chem., 1967, 32, 1751.

PREPARATION 5

7,8-Dimethyl-4,4a,5,6-tetrahydro-2(3H)-naphthalenone

To a stirred solution of lithium diisopropylamide (LDA) (22 mmol) in THF (200 ml) at −78° C. was added a solution of 2,3-dimethylcyclohexenone (2.48 g, 20 mmol) in THF (50 ml). The mixture was warmed to 25° C., and the solvent and the amine were removed under vacuum. The resulting solid was dissolved in THF (400 ml) and the solution cooled to −78° C. To this solution was added MVK (1.8 ml, 22 mmol) in THF (100 ml) over 10 min. The resulting mixture was stirred 12 hr at room temperature, then worked up. Removal of solvent yielded the dione as a yellow oil (2.8 g, 60%).

To a stirred solution of potassium 5-butoxide (t-BuOK) (0.56 g, 5 mmol) in tert-butyl alcohol (5-BuOH) (5 ml) and THF (80 ml) was added a solution of dione (0.388 g, 2 mmol) in THF (5 ml). After workup, the solvent was stripped affording the dienone (0.323 g, 91% yield) as an oil.
Ref: Tetrahedron, 1978, 34, 2439.

PREPARATION 6

1,4a-Dimethyl-7-isopropyl-4,4a,5,6-tetrahydro-2(3H)-naphthalenone 1,4a-Dimethyl-7-isopropyl-4,4a,5,6,7,8-hexahydro-10a-hydroxy-2(3H)-naphthalenone is prepared according to the procedure for Preparation 5 wherein carvone is substituted for 2,3-dimethylcyclohexenone, ethyl vinyl ketone is substituted for MVK, and 3N sodium ethoxide is substituted for LDA in THF. This hydroxy ketone is then refluxed with 10% aqueous oxalic acid for 8 hrs. to yield the dienone 6.
Ref: J. Org. Chem., 1964, 29, 2501.

PREPARATION 7

4,4a,5,6-Tetrahydro-2(3H)-naphthalenone

This material is prepared according to the procedure for Preparation 3 wherein 2-methoxy-2-methylchroman is substituted for 6-methyl-2-methoxy-2-methylchroman.
Ref: Tetrahedron Lett., 1971, 41, 3803.

PREPARATION 8

3-Methyl-4,6,7,8-tetrahydro-2(3H)-naphthalenone

This material is prepared according to the procedure for Preparation 5 wherein 2-hydroxycyclohexanone is substituted for 2,3-dimethylcyclohexenone, methylbutenone is substituted for MVK, and 2N KOH in MeOH is substituted fro LDA in THF.
Ref: Bull. Soc. Chim. France, 1962, 98.

PREPARATION 9

5-Methyl-4,6,7,8-tetrahydro-2(3H)-naphthalenone

To a mechanically stirred solution of 1,2,3,4-tetrahydro-6-methoxy-1-methyl-1-naphthalenol (31.7 g, 165 mmol) and absolute ethanol (315 ml) in liquid ammonia (1 L) was added sodium metal in pieces until the blue color persisted for several minutes. A total of 15 g sodium was added. The ammonia was allowed to evaporate overnight through a mercury bubbler, and the residue was poured into brine and extracted twice with ether. The combined ethereal extracts were vigorously stirred overnight with an equal volume of 10% aqueous HCl. Isolation of the crude product with ether afforded an orange-red oil which was chromatographed to yield 19.0 g (71%) of dienone 9.
Ref: J. Am. Chem. Soc., 1983, 105, 5679.

PREPARATION 10

6-Methyl-4,6,7,8-tetrahydro-2(3H)-naphthalenone

The reaction of MVK and 1-dimethylamino-4-methylcyclohexa-1,3-diene, followed by treatment with acid yields dienone 10.

Ref: JCS, Perkin I, 1973, 1757.

PREPARATION 11

1-Methyl-4,6,7,8-tetrahydro-2(3H)-naphthalenone

This material is prepared according to the procedure for Preparation 6 wherein 2-hydroxycyclohexanone is substituted for carvone. The resulting hydroxyketone is converted to the semicarbazone before dehydration with aqueous oxalic acid.

Ref: J. Am. Chem. Soc., 1953, 75, 3350.

PREPARATION 12

1,4a-Dimethyl-4,4a,5,6tetrahydro-2(3H)-naphthalenone

2-Methylcyclohexanone (99 g), sodium amide (18.4 g), and ether (150 ml) were stirred at room temp. under nitrogen for 4 hr. 1-Diethylaminopentan-3-one methiodide (135 g) in ethanol (60 ml) was added gradually and stirring continued for 4 hrs at room temp. and for 2 hrs at reflux. After addition of dilute HCl the solution was extracted (ether), dried, and distilled.

A portion of the hexahydroketonaphthalene (4.45 g) thus obtained was heated with N-bromosuccinimide (4.45 g) in $CCl_4$ (25 ml) and the mixture refluxed for 30 minutes. Succinimide (2.41 g) was removed from the cold solution and the residue refluxed with pyridine (10 ml) for 2 hrs to yield dienone 12.

Ref: JCS, 1952, 1437.

PREPARATION 13

7-Methoxy-4,4a,5,6-tetrahydro-2(3H)-naphthalenone

To a mixture of hexamethylphosphoramide (HMPA) (60 ml) and THF (15 ml) was added lithium (150 mg) in small pieces. The blue coloration of the metal solution developed after a few minutes and the temperature arose to 25° C. The solution was cooled to 0° C. and the stirring continued to 1.5 hr until almost all lithium was dissolved.

This mixture was added in portions to a solution of 2,7-dimethoxynaphthalene (0.5 g) in HMPA (20 ml), THF (20 ml), and EtOH (3 ml) at −45° C. After addition of THF (40 ml) the complete reaction mixture was stirred until decolorized (5 hr). The solution was then acidified with 2N HCl and extracted with ether (3×50 ml). After isolation, the enol was treated with HCl/MeOH under reflux to yield dienone 13.

Ref: J. Org. Chem., 1975, 40, 2841.

PREPARATION 14

3-Methoxy-4,4a,5,6-tetrahydro-2(3H)-naphthalenone

This material is prepared according to the procedure for Preparation 9 wherein 2,3-dimethoxynaphthalene is substituted for 1,2,3,4-tetrahydro-6-methoxy-1-methyl-1-naphthalenol.

Ref: Bull. Acad. Pol. Sci., Ser. Sci. Chim., 1972, 20, 15.

PREPARATION 15

4a-Carboethoxy-7-hydroxy-4,4a,5,6-tetrahydro-2(3H)-naphthalenone

This material is prepared according to the procedure for Preparation 6 wherein Hagemann's ester (ethyl 2-methyl-4-oxocyclohex-2-enyl-1-carboxylate) is substituted for carvone and ethyl 3-chloropropionate is substituted for ethyl vinyl ketone.

Ref: Tetrahedron Lett., 1966, 927.

PREPARATION 16

Dimethyl 4,4,7-trimethyl-4,4a,5,6-tetrahydro-2(3H)-naphthalenylidene malonate To $CH_2Cl_2$ (10 ml) at 0° C. and under $N_2$ was added titanium tetrachloride (5.2 mmol) dropwise. The dienone from Preparation 1 (2.6 mmol) and dimethyl malonate (3.1 mmol) in $CH_2Cl_2$ (5 ml) was then added dropwise. The mixture was stirred at 0° C. for 1 hr, then at room temperature for 1 hr. The reaction was quenched with water, taken up in ether, then washed with water, dried over $MgSO_4$, the solvent removed and the residue distilled or chromatographed to yield dimethyl 4,4,7-trimethyl-4,4a,5,6-tetrahydro-2(3H)-naphthalenylidene malonate in 90% yield. It has a peak absorption of 335 nm, and a K value of 108.

PREPARATION 17

Methyl-4,4,7-trimethyl-4,4a,5,6-tetrahydro-2(3H)-naphthalenylidene cyanoacetate A mixture of the ketone of Preparation 1 (10 mmol), methylcyanoacetate (12 mmol) piperidine (0.5 mmol), and hexanoic acid (0.5 mmol) in cyclohexane (7 ml) was refluxed for 24–48 hours while water was removed with a Dean-Stark trap. After cooling, the mixture was diluted with ether, washed with brine, dried over magnesium sulfate, and the solvent removed. The residue was chromatographed to yield the cyanoacetate ester in yields of 75–90 percent. It has a peak absorption of 366 nm and a K value of 143.

PREPARATION 18

4,4,7-Trimethyl-4,4a,5,6-tetrahydro-2(3H)-naphthalenylidene acetonitrile

A mixture of the cyanoacetate from Preparation 17 (3.7 mmol) and lithium amide (100 mg) in 1-heptanol (10 ml) was refluxed for 2 hours. After cooling, the mixture was diluted with ether, washed with water, dried over magnesium sulfate, and the solvent removed. The product was purified by chromatography and had a peak absorption of 320 nm and a K value of 152.

PREPARATION 19

Diethyl 4,4,7-trimethyl-4,4a,5,6-tetrahydro-2(3H)-naphthalenylidene malonate This material is prepared according to the procedure for Preparation 16 wherein diethyl malonate is substituted for dimethyl malonate. This material has a peak absorption of 333 nm and a K value of 91.

PREPARATION 20

4,4,7-Trimethyl-4,4a,5,6-tetrahydro-2(3H)-naphthalenylidene malonic acid

A mixture of the diester from Preparation 19 (3.0 mmol) and potassium hydroxide (340 mg) in methanol (5 ml) and water (5 ml) was refluxed for 20 hours. The mixture was then poured into water and extracted with ether. The aqueous phase was acidified with ice cold hydrochloric acid, extracted with ether, the organic phase dried over magnesium sulfate, and the solvent removed. Recrystallization yields the product with a peak absorption of 329 nm and a K value of 118.

PREPARATION 21

Ethyl 7-methyl-4,4a,5,6-tetrahydro-2(3H)-naphthalenylidene acetate

A mixture of the dienone from Preparation 2 (1.6 mmol), ethylbromacetate (2.7 mmol), zinc (8 g) and iodine (200 mg) in ether (40 ml) and cyclohexane (40 ml) was refluxed for 16 hours. The mixture was diluted with methanol, filtered, then added to ice cold 6N hydrochloric acid. After extraction with ether, the organic layer was dried over magnesium sulfate, the solvent removed, and the residue chromatographed to yield the ester in 46% yield. It has a peak absorption of 322 nm and a K value of 140.

PREPARATION 22

4,4,7-Trimethyl-4,4a,5,6-tetrahydro-2(3H)-naphthalenylidene malononitrile

This material is prepared according to the procedure for Preparation 17 wherein malononitrile is substituted for methylcyanoacetate. This material has a peak absorption of 364 nm and a K value of 138.

PREPARATION 23

Dimethyl 7-methyl-4,4a,5,6-tetrahydro-2(3H)-naphthalenylidene malonate

This material is prepared according to the procedure for Preparation 16 wherein the dienone of Preparation 2 is substituted for the dienone of Preparation 1. It has a peak absorption of 334 nm and a K value of 126.

PREPARATION 24

Diethyl 7-methyl-4,4a,5,6-tetrahydro-2(3H)-naphthalenylidene malonate

This material is prepared according to the procedure for Preparation 19 wherein the dienone of Preparation 2 is substituted for the dienone of Preparation 1. It has a peak absorption of 334 nm and a K value of 119.

PREPARATION 25

Dimethyl 1,4a-dimethyl-7-isopropyl-4,4a,5,6-tetrahydro-2(3H)-naphthalenylidene malonate This material could be prepared according to the procedure for Preparation 16 wherein the dienone of preparation 6 is substituted for the dienone of Preparation 1.

Preparation 26

Methyl 1,4a-dimethyl-7-isopropyl-4,4a,5,6-tetrahydro-2(3H)-naphthalenylidene cyanoacetate This material could be prepared according to the procedure for Preparation 17 wherein the dienone of Preparation 6 is substituted for the dienone of Preparation 1.

PREPARATION 27

1,4a-Dimethyl-7-isopropyl-4,4a,5,6-tetrahydro-2(3H)-naphthalenylidene acetonitrile This material could be prepared according to the procedure for Preparation 18 wherein the cyanoacetate of Preparation 26 is substituted for the cyanoacetate of Preparation 17.

PREPARATION 28

1,4a-Dimethyl-7-isopropyl-4,4a,5,6-tetrahydro-2(3H)-naphthalenylidene malonic acid This material could be prepared according to the procedure for Preparation 20 wherein the diester of Preparation 25 is substituted for the diester of Preparation 19.

PREPARATION 29

Ethyl 1,4a-dimethyl-7-isopropyl-4,4a,5,6-tetrahydro-2(3H)-naphthalenylidene acetate This material could be prepared according to the procedure for Preparation 21 wherein the dienone of Preparation 6 is substituted for the dienone of Preparation 2.

PREPARATION 30

1,4a-Dimethyl-7-isopropyl-4,4a,5,6-tetrahydro-2(3H)-naphthalenylidene malononitrile This material could be prepared according to the procedure for Preparation 22 wherein the dienone of Preparation 6 is substituted for the dienone of Preparation 1.

PREPARATION 31

Dimethyl 5-methyl-4,6,7,8-tetrahydro-2(3H)-naphthalenylidene malonate

This material could be prepared according to the procedure for Preparation 16 wherein dienone of Preparation 9 is substituted for the dienone of Preparation 1.

PREPARATION 32

Methyl 5-methyl-4,6,7,8-tetrahydro-2(3H)-naphthalenylidene cyanoacetate

This material could be prepared according to the procedure for Preparation 17 wherein the dienone of Preparation 9 is substituted for the dienone of Preparation 1.

PREPARATION 33

5-Methyl-4,6,7,8-tetrahydro-2(3H)-naphthalenylidene acetonitrile

This material could be prepared according to the procedure for Preparation 18 wherein the cyanoacetate of Preparation 32 is substituted for the cyanoacetate of Preparation 17.

PREPARATION 36

5-Methyl-4,6,7,8-tetrahydro-2(3H)-naphthalenylidene malononitrile

This material could be prepared according to the procedure for Preparation 22 wherein the dienone of Preparation 9 is substituted for the dienone of Preparation 1.

TABLE A

| | EXAMPLES OF FORMULA I | | | | | | | | | | | |
|---|---|---|---|---|---|---|---|---|---|---|---|---|
| Prep No. | $R^1$ | $R^2$ | $R^3$ | $R^4$ | $R^5$ | $R^6$ | $R^7$ | $R^8$ | $R^9$ | $R^{10}$ | $R^{11}$ | Olefin |
| 1 | H | H | $CH_3$ | $CH_3$ | H | H | H | H | $CH_3$ | H | H | a |
| 2 | H | H | H | H | H | H | H | H | $CH_3$ | H | H | a |
| 3 | H | H | H | H | H | H | $CH_3$ | H | H | H | H | a |
| 4 | H | H | H | H | $CH_3$ | H | H | H | H | H | H | a |
| 5 | H | H | H | H | H | H | H | H | $CH_3$ | $CH_3$ | H | a |
| 6 | H | H | H | H | $CH_3$ | H | H | H | $C_3H_7$ | H | $CH_3$ | a |
| 7 | H | $CH_3$ | H | H | H | H | H | H | H | H | H | a |
| 8 | $CH_3$ | H | H | H | H | H | H | H | H | H | H | b |
| 9 | H | H | H | H | H | $CH_3$ | H | H | H | H | H | b |
| 10 | H | H | H | H | H | H | $CH_3$ | H | H | H | H | b |
| 11 | H | H | H | H | H | H | H | H | H | H | $CH_3$ | b |
| 12 | H | H | H | H | $CH_3$ | H | H | H | H | H | $CH_3$ | a |
| 13 | H | H | H | H | H | H | H | H | $OCH_3$ | H | H | a |
| 14 | H | $OCH_3$ | H | H | H | H | H | H | H | H | H | a |
| 15 | H | H | H | H | COOEt | H | H | H | OH | H | H | a |

TABLE B

| | EXAMPLES OF FORMULA II | | | | | | | | | | | | |
|---|---|---|---|---|---|---|---|---|---|---|---|---|---|
| Prep. No. | $R^1$ | $R^2$ | $R^3$ | $R^4$ | $R^5$ | $R^6$ | $R^7$ | $R^8$ | $R^9$ | $R^{10}$ | $R^{11}$ | Olefin | X | Y |
| 16 | H | H | $CH_3$ | $CH_3$ | H | H | H | H | $CH_3$ | H | H | a | $COOCH_3$ | $COOCH_3$ |
| 17 | H | H | $CH_3$ | $CH_3$ | H | H | H | H | $CH_3$ | H | H | a | CN | $COOCH_3$ |
| 18 | H | H | $CH_3$ | $CH_3$ | H | H | H | H | $CH_3$ | H | H | a | CN | H |
| 19 | H | H | $CH_3$ | $CH_3$ | H | H | H | H | $CH_3$ | H | H | a | COOEt | COOet |
| 20 | H | H | $CH_3$ | $CH_3$ | H | H | H | H | $CH_3$ | H | H | a | COOH | COOH |
| 21 | H | H | H | H | H | H | H | H | $CH_3$ | H | H | a | H | COOEt |
| 22 | H | H | $CH_3$ | $CH_3$ | H | H | H | H | $CH_3$ | H | H | a | CN | CN |
| 23 | H | H | H | H | H | H | H | H | $CH_3$ | H | H | a | $COOCH_3$ | $COOCH_3$ |
| 24 | H | H | H | H | H | H | H | H | $CH_3$ | H | H | a | COOEt | COOEt |
| 25 | H | H | H | H | $CH_3$ | H | H | H | $C_3H_7$ | H | $CH_3$ | a | $COOCH_3$ | $COOCH_3$ |
| 26 | H | H | H | H | $CH_3$ | H | H | H | $C_3H_7$ | H | $CH_3$ | a | CN | $COOCH_3$ |
| 27 | H | H | H | H | $CH_3$ | H | H | H | $C_3H_7$ | H | $CH_3$ | a | CN | H |
| 28 | H | H | H | H | $CH_3$ | H | H | H | $C_3H_7$ | H | $CH_3$ | a | COOH | COOH |
| 29 | H | H | H | H | $CH_3$ | H | H | H | $C_3H_7$ | H | $CH_3$ | a | H | COOEt |
| 30 | H | H | H | H | $CH_3$ | H | H | H | $C_3H_7$ | H | $CH_3$ | a | CN | CN |
| 31 | H | H | H | H | H | $CH_3$ | H | H | H | H | H | b | $COOCH_3$ | $COOCH_3$ |
| 32 | H | H | H | H | H | $CH_3$ | H | H | H | H | H | b | CN | $COOCH_3$ |
| 33 | H | H | H | H | H | $CH_3$ | H | H | H | H | H | b | CN | H |
| 34 | H | H | H | H | H | $CH_3$ | H | H | H | H | H | b | COOH | COOH |
| 35 | H | H | H | H | H | $CH_3$ | H | H | H | H | H | b | H | COOEt |
| 36 | H | H | H | H | H | $CH_3$ | H | H | H | H | H | b | CN | CN |

PREPARATION 34

5-Methyl-4,6,7,8-tetrahydro-2(3H)-naphthalenylidene malonic acid

This material could be prepared according to the procedure for Preparation 20 wherein the diester of Preparation 31 is substituted for the diester of Preparation 19.

PREPARATION 35

Ethyl 5-methyl-4,6,7,8-tetrahydro-2(3H)-naphthalenylidene acetate

This material could be prepared according to the procedure for Preparation 21 wherein the dienone of Preparation 9 is substituted for the dienone of Preparation 2.

It has been established that actinic radiation between 290 nm and 320 nm produces substantially all the burning or erythemal energy and a substantial portion of the tanning energy, while the radiation between 320 nm and 400 nm produces incident tanning and minor burning. The cosmetic industry has divided these spectra into the burning range UV-B (290–320 nm) and the tanning range UV-A (320–400 nm). Since approximately 76% of the physiological tanning potential of sunlight is found in the UV-B range and the balance is found in the UV-A range, it is desireable to have a substantial amount of the radiation in both ranges filtered out before it produces a harmful effect on the surface of human skin. While sunscreen lotions have been formulated to be most effective in the UV-B range more recent studies have indicated that it is desireable to have collective adsorption in the UV-A range was well. It has been difficult to find a practical compound which effectively absorbs in both ranges. Therefore, formulators must resort to the combination of two compounds which are each effective either in the UV-B, or UV-A range to provide maximum skin protection. No single compound falling within the definition of formula I is effective over the entire 290–400 nm range and therefore two or more compounds can be selected and blended within the formulation at varying concentrations at the desired balance between burning and tanning is accommodated. Such a combination is shown in Examples 5, 6, 7, 12, 13, 14, 15 and 16. It is preferred to have a formulation having at least one compound which absorbs in the 290–320 nm range and at least one other which absorbs in the 320–400 nm range. At least one is selected from formulas I and II.

The use of the UV filters of the invention can be demonstrated in lotion formulations which are topically applied to the surface of the skin. The effectiveness of the UV light absorbers are tested on human subjects by treating a 1 cm square section of a subject's back with predetermined amounts of lotion, exposing the treated areas to UV light for a set period of time and thereafter making a visual comparison with untreated and fully masked skin areas. The SPF (skin protection factor) is calculated by comparing the effects of radiation on protected skin with the unprotected skin of warm blooded animals.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1–4 and controls all ingredients can be mixed together and stirred in conventional apparatus. Since in many cases a single compound used at a reasonable concentration does not effectively protect throughout the whole region of the earth reaching solar UV spectrum, blends of two or more UV absorbers can be used in a formulation to afford greater protection.

TABLE 1

| SUNSCREEN FORMULAS | | | | |
|---|---|---|---|---|
| | Examples (% by weight) | | | |
| | (1) | (2) | (3) | (4) |
| (A) | | | | |
| Preparation 16 | 5 | 2 | 5 | 2 |
| Mineral Oil (Carnation) | 5 | 5 | 0 | 0 |
| Stearyl Alcohol | .5 | .5 | 0 | 0 |
| Cetyl Alcohol | .5 | .5 | 0 | 0 |
| Silicone Oil SF-96, 350 cs | .5 | .5 | 0 | 0 |
| Polyoxyethylene (21) Stearyl ether/Brij ® 721 | 2.2 | 2.28 | 0 | 0 |
| Polyoxyethylene (2) stearyl ether/Brij ® 721 | 1.8 | 1.72 | 0 | 0 |
| (B) | | | | |
| Water (deionized) | 73.95 | 221.85 | 0 | 0 |
| Carbopol ® 934, 2% soda | 10 | 30 | 0 | 0 |
| (C) | | | | |
| Sodium Hydroxide | 0.2 | 0.2 | 0 | 0 |
| (D) | | | | |
| DNDNH-55 (Glyco ®) | 0.35 | 0.35 | 0 | 0 |
| (E) | | | | |
| Dimethyl Isosorbide | 0 | 0 | 95 | 98 |
| Physical Form | thin | cream | clear | clear |

TABLE 1-continued

| SUNSCREEN FORMULAS | | | | |
|---|---|---|---|---|
| | Examples (% by weight) | | | |
| | (1) | (2) | (3) | (4) |
| | cream | | liquid | liquid |

Procedure Examples 1 & 2: Blend ingredients (A) and heat to 70° C. Separately Blend ingredients (B) heat to 75° C. add to (A). Add (C) to (AB) and cool to 40° C. Add (D) with stirring. Preparation 16 is readily soluble in dimethylisosorbide.

The solution of Example 3 was tested to determine the skin protection factor in the UV-A and UV-B range of ultra-violet light on eight specimens of excised hairless mouse epidermis. The skin was coated at the level of 1 mg/cm. An average SPF value in each range is listed in Table 2.

TABLE 2

| | SUNSCREEN FORMULAS | | | | |
|---|---|---|---|---|---|
| Peak Absortion (nm) | Molar Extinction Coeff mol. weight | SPF | | Standard Revistion | |
| | | UV-A | UV-B | UV-A | UV-B |
| 334 | 98.5 | 3.27 | 2.53 | .53 | .85 |
| Control dimethyl isosorbide 100% | | <1.0 | <1.0 | | |

Lotions are tested in vivo on female subjects ranging from ages 27–50 having skin type I (always burns easily, never tans), type II (always burns easily, tans minimally) and type III (burns moderately, tans gradually). Each subject is exposed to UV radiation on 3 separate days at 27, 28 and 29 (mW/cm$^2$) respectively. Templates are applied to individual skin sites on designated areas of the back. Application of the test material is made by uniformly spreading the lotion or cream over a 50 cm$^2$ area (3.5 cm by 14.3 cm) at a dose of 2 mg/cm$^2$ with a finger cot. Approximately 15 minutes after application the sites are irradiated. Test sites are scored approximately 24 hours after exposure.

The minimum erythema dose (MED) for each treatment and each subject is determined and compared with the MED for unprotected skin. The SPF is determined for each example by the following formula SPF=[MED (protected skin)/MED (unprotected skin)].

In addition to their use in coating skin surfaces to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and may be used singly or in combination to provide a wider range of protection. The following formulations are given to demonstrate a few of the many applications.

| Example No. | Filtering Agent | Carrier Ingredients | Composition (% by Wt) |
|---|---|---|---|
| 5 | Aerosol Hairdressing | | |
| | Prep 16 | | 2.0 |
| | Prep 3 | | 3.0 |
| | | Decaglycerol monolaurate | 2.0 |

| Example No. | Filtering Agent | Carrier Ingredients | Composition (% by Wt) |
|---|---|---|---|
| | | Polyoxypropylene (200) monooleate | 3.0 |
| | | Ethoxylated (10) lanolin alcohols | 1.0 |
| | | Propylene glycol | 2.0 |
| | | Ethyl alcohol, anhydrous | 39.5 |
| | | Protein polypeptide (20% alcoholic) | 1.2 |
| | | Isopropyl myristate | 1.3 |
| | | Propellant 11 | 15.0 |
| | | Propellant 12 | 30.0 |
| | | Water | q.s. |

Procedure for Formula: Dissolve all ingredients in slightly warmed ethylalcohol, avoiding loss of the alcohol, add the water, and agitate well to disperse any haze. Filter the concentrate and fill into aerosal containers. Add propellants.

| Example No. | Filtering Agent | Carrier Ingredients | Composition (% by Wt) |
|---|---|---|---|
| 6 | Formula for Creamy Type Lipstick Base | | |
| | Prep 17 | | 3 |
| | Prep 8 | | 5 |
| | | Carnauba wax | 3 |
| | | Candelilla wax | 7 |
| | | Ozokerite ® | 3 |
| | | Beeswax | 7 |
| | | Lanolin | 10 |
| | | Castor oil | 57 |
| | | Isopropyl myristate | 5 |
| | | Perfume | q.s. |
| 7 | Water-In-Oil (W/O), Detergent Resistant, Liquid Auto Polish | | |
| | Part A | 2.00% Durmont ® 500 Montan Wax | (Dura Commodities) |
| | Part B | 0.75% DC 530 Silicone Fluid | (Dow Corning) |
| | | 4.25% DC 531 Silicone Fluid | |
| | | 1.50% SPAN ® 80 | |
| | | 10.00% Kerosene | |
| | | 16.50% Stoddard Solvent | |
| | | 5.0% Preparation 5 | |
| | | 5.0% Preparation 27 | |
| | Part C | 10.00% Kaopolite ® SFO | (Kaopolite) |
| | Part D | 45.00% Water | |
| | | Method of Preparation: | |
| | 1. Melt wax in Part A (85–90° C.) | | |
| | 2. Add Part B ingredients to melted wax and stir to blend well. Return temperature to 85–90° C. | | |
| | 3. Add Part C to Part A/Part B blend and mix until uniform with medium agitation. Keep temperature in the 85–90° C. range. | | |
| | 4. Heat Part D to 95° C. and slowly add to the blend with high speed stirring until emulsion is obtained. | | |
| | 5. Cool to 40–45° C. with continuous stirring. | | |
| | 6. Homogenize. | | |

| Example No. | Filtering Agent | Carrier Ingredients | Composition (% by Wt) |
|---|---|---|---|
| 8 | Neutral Base Lacquer | | |
| | Materials | | Pounds |
| | Urethane 60% N.V. | | 32 |
| | Long oil alkyd 60% N.V. | | 352 |
| | Triton ® X-45 | | 7.5 |
| | Nuxtra Calcium 6% | | 12 |
| | Bentone Jell 8% | | 28 |
| | Disperse the bentone jell under high speed cowles and add: | | |
| | Preparation 1 | | 16 |
| | Low odor mineral spirits | | 85 |
| | Cyclodex cobalt 6% | | 3 |
| | JK 270-70% | | 76 |
| | Water | | 205 |
| | Anti skin | | 2 |
| | Viscosity: | 80–85 KU | |
| | W/G: | 7.84 | |
| | 60° Gloss: | 85 | |
| | SAG: | 6 ml | |
| 9 | O/W Paraffin Wax Emulsion | | |
| | Part A | 50% Paraffin wax | |
| | | 5% SPAN ® 60/TWEEN ® 60 (50/50) | |
| | | 5% Preparation 6 | |
| | Part B | 40% Water | |
| | | Method of Preparation: | |
| | 1. Melt Part A ingredients together and heat to 80° C. | | |
| | 2. Heat Part B to 85° C. | | |
| | 3. Add Part B to Part A slowly with moderate agitation until inversion occurs. Add remaining water rapidly. | | |
| | 4. Cool in cold water bath with slow agitation to approximately 35° C. | | |
| 10 | O/W Soft Microcrystalline Wax Emulsion | | |
| | Part A | 30% Microcrystalline wax (Ultraflex ® Amber Wax-Petrolite Corp.) | |
| | | 30% SPAN ® 60/TWEEN ® 60 (78/22) | |
| | | 5% Preparation 2 | |
| | Part B | 62% Water | |
| | | Method of Preparation: | |
| | 1. Melt together Part A ingredients and heat to 80–90° C. | | |
| | 2. Heat Part B to boiling. | | |
| | 3. Add Part B to Part A slowly with moderate agitation until inversion occurs. Add remaining water rapidly. | | |
| | 4. Remove from heat and cool to room temperature without stirring. | | |
| 11 | O/W Carnauba Wax Emulsion | | |
| | Part A | 10% Carnauba wax | |
| | | 3% TWEEN ® 80 | |
| | | 5% Preparation 1 | |
| | Part B | 82% Water | |
| | | Method of Preparation: | |
| | 1. Melt Part A ingredients together and heat to 95° C. and hold. | | |
| | 2. Heat Part B to boiling. | | |
| | 3. Add Part B to Part A slowly with moderately fast stirring until inversion occurs. Add remaining water rapidly. | | |
| | 4. Remove emulsion from heat and cool rapidly with stirring. | | |

SUNSCREEN LOTION

Example 12

| PHASE | INGREDIENTS (SUPPLIERS) | PERCENT BY WEIGHT |
|---|---|---|
| A | Petrolatum, Snow White ® USP (Ruger) | 35.00 |

-continued

| PHASE | INGREDIENTS (SUPPLIERS) | PERCENT BY WEIGHT |
|---|---|---|
| | Brij 721 (ICI) | 1.16 |
| | Brij 72 (ICI) | 3.86 |
| | Silicone Oil, 350 cs (Ruger) | 3.00 |
| | Preparation 3 | 5.00 |
| | Uvinul ® M-40 (BASF) | 3.00 |
| B | Water | 48.08 |
| | Carbopol ® 934 (B. F. Goodrich) | 0.40 |
| C | Sodium Hydroxide (10% Aqueous Solution) | 0.40 |
| D | Dowicil ® 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

Example 13

| PHASE | INGREDIENTS (SUPPLIERS) | PERCENT BY WEIGHT |
|---|---|---|
| A | Arlamol ® E (ICI) | 7.00 |
| | Stearyl Alcohol | 2.50 |
| | Silicone Oil, 350 cs (Ruger) | 5.00 |
| | Arlasolve ® 200 (ICI) | 2.10 |
| | Brij ® 72 (ICI) | 4.90 |
| | Preparation 1 | 5.00 |
| | Preparation 16 | 3.00 |
| B | Water | 70.00 |
| | Carbopol ® 934 (B. F. Goodrich) | 0.20 |
| C | Sodium Hydroxide (10% Aqueous Solution) | 0.20 |
| D | Dowicil ® 200 (DOW) | 0.10 |
| Preparation: | Heat (A) to 65° C. Heat (B) to 70° C. Add (B) to (A) slowly with moderate agitation. Add (C). Cool to 50° C. Add (D). Cool, while stirring to 35° C. | |

SUNSCREEN LOTION

Example 14

| PHASE | INGREDIENTS (SUPPLIERS) | PERCENT BY WEIGHT |
|---|---|---|
| A | Arlamol ® E (ICI) | 7.00 |
| | Stearyl Alcohol | 2.50 |
| | Silicone Oil, 350 cs (Rugher) | 5.00 |
| | Arlasolve ® 200 (ICI) | 2.10 |
| | Brij ® 72 (ICI) | 4.90 |
| | Preparation 19 | 3.00 |
| | Arlaton UVB (ICI) | 5.00 |
| B | Water | 70.00 |
| | Carbopol 934 (B. F. Goodrich) | 0.20 |
| C | Sodium Hydroxide (10% Aqueous Solution) | 0.20 |
| D | Dowicil ® 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

Example 15

| PHASE | INGREDIENTS (SUPPLIERS) | PERCENT BY WEIGHT |
|---|---|---|
| A | Petrolatum, Snow White USP (Ruger) | 30.00 |
| | Brij ® 721 (ICI) | 1.16 |
| | Brij ® 72 (ICI) | 3.86 |
| | Preparation 18 | 4.00 |
| | Preparation 23 | 4.00 |
| | Methyl 3-methyl-2-cyclohexenyli-cyanoacetate | 4.00 |
| | Silicone Oil, 350 cs (Ruger) | 3.00 |
| B | Water | 49.08 |
| | Carbopol ® 934 (B. F. Goodrich) | 0.40 |
| C | Sodium Hydroxide (10% Aqueous Solution) | 0.40 |
| D | Dowicil ® 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

Example 16

| PHASE | INGREDIENTS (SUPPLIERS) | PERCENT BY WEIGHT |
|---|---|---|
| A | Arlamol ® E (ICI) | 7.00 |
| | Stearyl Alcohol | 2.50 |
| | Silicone Oil, 350 cs (Ruger) | 5.00 |
| | Arlasolve ® 200 (ICI) | 2.10 |
| | Brij ® 72 (ICI) | 4.90 |
| | Preparation 25 | 4.50 |
| | Methyl 3,5,5,-Trimethyl-2-Cyclohexenylidene Cyanoacetate | 5.50 |
| B | Water | 68.0 |
| | Carbopol ® 934 (B. F. Goodrich) | 0.20 |
| C | Sodium Hydroxide (10% Aqueous Solution) | 0.20 |
| D | Dowicil ® 200 (DOW) | 0.10 |
| Preparation: | Heat (A) to 65° C. Heat (B) to 70° C. Add B to A slowly with moderate agitation. Add (C). Cool to 50° C. Add (D). Cool, while stirring to 35° C. | |

What is claimed is:

1. A compound of the formula:

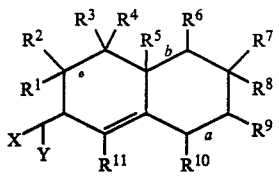

wherein:

X and Y are independently selected from —H, —CN, —COOR$^{12}$, —CONHR$^{12}$, —CON(R$^{12}$)$_2$, —PhCOOR$^{12}$, —PhCOR$^{12}$, —PhOR$^{12}$, —PhN(R$^{12}$)$_2$, [or wherein only one X or Y is substituted by —H,] provided that only one of X and Y can be —H; and R$^1$–R$^{11}$ are selected from H, —OH, —COOR$^{12}$, alkyl, alkoxy, or hydroxyalkyl groups having 1-5 carbon atoms and R$^{12}$ is selected from H, alkyl, alkylaryl or arylalkyl groups of 1-22 carbon atoms, and Ph is a benzene ring; and wherein one of a and b is a double bond and the other is a single bond.

2. A compound in accordance with claim 1 wherein X and Y are selected from the group consisting of —CN, —COOR$^{12}$ or —COR$^{12}$.

3. A compound in accordance with claim 1 wherein X and Y are selected from —COOR$^{12}$.

4. A compound in accordance with claim 1 wherein X and Y are —CO$_2$CH$_3$; R$^1$, R$^2$, R$^5$, R$^6$, R$^7$, R$^8$, R$^{10}$, and R$^{11}$ are H; R$^3$, R$^4$, R$^9$ and R$^{12}$ are —CH$_3$; and the olefin confirmation is (a).

* * * * *

UNITED STATES PATENT AND TRADEMARK OFFICE
CERTIFICATE OF CORRECTION

PATENT NO. : 4,889,947
DATED : December 26, 1989
INVENTOR(S) : Charalambos J. Phalangas et al It is certified that error appears in the above-identified patent and that said Letters Patent is hereby corrected as shown below:

At column 5, line 46, delete the word "arose" and substitute therefor the word --rose--.

At column 10, line 65, delete the phrase "was well" and substitute therefor the phrase --as well--.

In claim 1, column 17, lines 4-10, the formula should read:

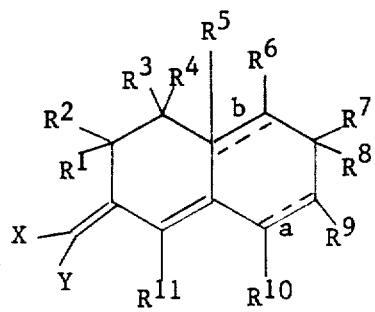

Signed and Sealed this

Twenty-eighth Day of January, 1992

Attest:

HARRY F. MANBECK, JR.

Attesting Officer

Commissioner of Patents and Trademarks